US005971181A

United States Patent [19]

Niedospial, Jr. et al.

[11] Patent Number: 5,971,181

[45] Date of Patent: Oct. 26, 1999

[54] MULTIPLE USE UNIVERSAL STOPPER

[75] Inventors: John J. Niedospial, Jr., Burlington, N.J.; Mark E. Gabbard; Timothy J. Gabbard, both of Salisbury, Md.

[73] Assignee: Brocco Research USA Inc., Princeton, N.J.

[21] Appl. No.: 09/080,091

[22] Filed: May 16, 1998

Related U.S. Application Data

[63] Continuation-in-part of application No. 09/071,944, May 4, 1998.

[51] Int. Cl.[6] ............................ A61B 19/00; B65D 51/20

[52] U.S. Cl. .................................... 215/247; 215/DIG. 3; 604/415

[58] Field of Search .................................... 215/247, 248, 215/249, DIG. 3, 355, 277; 604/403, 415, 411

[56] References Cited

U.S. PATENT DOCUMENTS

| | | | |
|---|---|---|---|
| 2,289,677 | 7/1942 | Perelson . | |
| 2,326,490 | 8/1943 | Perelson . | |
| 2,342,215 | 2/1944 | Perelson . | |
| 2,667,986 | 2/1954 | Perelson . | |
| 3,872,992 | 3/1975 | Larson . | |
| 3,940,003 | 2/1976 | Larson . | |
| 3,977,555 | 8/1976 | Larson . | |
| 4,412,623 | 11/1983 | Schmidt . | |
| 5,060,812 | 10/1991 | Ogle, II | 215/247 |
| 5,100,010 | 3/1992 | Waters | 215/247 X |
| 5,114,030 | 5/1992 | Conard | 215/249 |
| 5,232,109 | 8/1993 | Tirrell et al. . | |
| 5,361,921 | 11/1994 | Burns | 215/247 X |
| 5,364,386 | 11/1994 | Fukuoka et al. . | |
| 5,429,256 | 7/1995 | Kestenbaum . | |
| 5,433,330 | 7/1995 | Yatsko et al. . | |
| 5,451,374 | 9/1995 | Molina | 215/249 X |
| 5,454,805 | 10/1995 | Brony | 215/DIG. 3 X |
| 5,464,111 | 11/1995 | Vacek et al. | 215/249 |
| 5,702,019 | 12/1997 | Grimard | 215/DIG. 3 X |
| 5,785,691 | 7/1998 | Vetter et al. | 215/DIG. 3 X |
| 5,833,089 | 11/1998 | Manni et al. | 215/249 |

*Primary Examiner*—Stephen K. Cronin
*Assistant Examiner*—Nathan Newhouse
*Attorney, Agent, or Firm*—Imre Balogh

[57] ABSTRACT

Universal closure assembly designed for use in various containers having a fluid port for access to the content of the container. The universal closure assembly incorporates an elastomeric membrane capable of being ruptured by an access means such as a luer connector or a syringe having a sharp or blunt cannula or a sharp or blunt spike for fluid communication between the content of the container and the access means. The elastomeric membrane reseals itself after being ruptured by an access means.

22 Claims, 16 Drawing Sheets

MULTIPLE USE UNIVERSAL STOPPER

This application is a continuation-in-part of application Ser. No. 08/071,944, filed on May 4, 1998.

BACKGROUND OF THE INVENTION

1. Field of the Invention

This invention relates to an elastomeric stopper having a self-sealing means so that a pharmaceutical fluid contained in a container closed by the elastomeric stopper can be repeatedly accessed by the use of a luer connector or a syringe having a blunt or sharp needle cannula.

2. Reported Developments

The prior art has developed numerous devices to prevent accidental needle strike injuries to practitioners and patients. Such injuries are known to spread infectious diseases including hepatitis and AIDS. One of the main features of these devices is the lack of exposed sharp needles. The closures or stoppers have built in access means to the content of the containers, such as vials, cartridges and bottles. The closures or stoppers in these devices serve the dual function of hermetically sealing the container while allowing access to the content therethrough.

Stopper systems for containers such as vials and bottles are made of materials that are resistant to chemicals and pharmaceuticals such as corrosive materials, reagents, parenteral solutions and solid formulations reconstitutable with a solvent prior to use. The most commonly used stopper/container system for such products has been glass or plastic bottles and vials equipped with stoppers made of elastomeric materials. The system provides for good hermetical seal, safe storage and easy access to the content through the elastomeric stopper via the use of an infusion spike or a syringe when withdrawal of the content is desired. The elastomeric stopper used generally comprises an elastomeric base, such as natural or synthetic rubber and an inert coating covering at least some portions of the stopper. The coating used includes chlorobutyl rubber, polymeric fluorocarbon resins such as polytetrafluoroethylene and various thermoplastic films. The coating is intended to insulate the elastomeric stopper base from the contents of the container in order to prevent contact and possible chemical reactions therebetween.

Generally, the elastomeric stopper is of cylindrical shape and has a flange head portion overlying the open top end of the container. Integral with the head portion is a body portion which extends into the open end and seated in the neck portion of the container, the diameter of the body portion being somewhat larger than the inside diameter of the container so that a tight seal is created between the body portion and the wall of the container. The lower end of the body portion is beveled towards the central, longitudinal axis of the body portion to facilitate the insertion of the body portion into the container. The circular bottom surface that faces the contents of the container is substantially planar and is imperforate, having no recess therein. The head portion of the stopper is provided with a central recess extending downwardly from the top thereof a substantial distance into the body portion so that the central recess and the circular bottom surface define a diaphragm. The walls forming the recess are generally cylindrical but may be provided with one or more circular protuberances extending inwardly to terminate just short of the center line of the stopper. The circular protuberances serve to press against and hold the needle of a syringe when the needle is inserted through the recess to penetrate the diaphragm for removal of the contents of the container. The elastomeric stopper is held in position by a metal ring or cap usually constructed of aluminum. The metal ring or cap has a removable center opening for allowing insertion of the syringe needle into the container.

Another type of the prior art stoppers has the needle penetrable diaphragm on the top portion of the stopper.

Various stopper and access systems exist in the prior art to hold and remove the contents of containers which are illustrated hereunder.

U.S. Pat. Nos. 2,289,677 and 2,326,490 disclose a rubber stopper for use in vials comprising: an outer wall which serves as a seal between the vial and the stopper; and an inner wall forming a chamber in the center of the stopper, the bottom portion of the inner wall serving as a diaphragm. A hollow needle, having a sharp end for piercing the diaphragm, and an outer end exposed for connection with a syringe, is carried by the outer wall. A syringe connected to the outer end of the needle and pushed inwardly effects piercing of the diaphragm thereby permitting aspiration of the contents of the vial.

U.S. Pat. No. 2,342,215 discloses a dispensing and sealing stopper for a vial comprising: a stopper body having a hollow needle therein, one end of said hollow needle is in constant communication with the contents of the vial, and the other end is sealed by a penetrable, thin membrane. When withdrawal of the contents of the vial is desired, a syringe is inserted into the stopper to penetrate the thin membrane and to engage the other end of the hollow needle. When the syringe is removed, the thin membrane self-closes to maintain the hollow needle and the contents of the vial sterile.

U.S. Pat. No. 5,232,109 discloses an elastomeric stopper for a bottle, said stopper includes an annular protuberance which forms a second seal with the shaft of a spike inserted in the stopper to prevent leakage, blow-out and introduction of particulate matter into the fluid-containing bottle.

U.S. Pat. No. 5,364,386 relates to an infusion unit which comprises: a flexible, large container, a small medicine vial and a pipe which serves to communicate between the large, flexible container and the small medicine vial.

The large container is adapted to hold a solvent or diluent, while the medicine vial contains a powdery medicine which is to be mixed and dissolved in the solvent or diluent contained in the large, flexible container. Upon dissolution, the mixed medicine is discharged through an outlet at the lower end of the large container for infusion into a patient.

U.S. Pat. No. 5,429,256 pertains to a drug withdrawal system for a vial. The withdrawal system comprises: a vial containing a medicament therein and closed with a rubber gasket; and an apparatus which snap fits on top of the vial. The apparatus comprises: a chassis and a cap which is attached to the cap by a living hinge.

The chassis is cylindrical and has vertical grooves on the external sides to facilitate handling. The top of the chassis has a central opening. The chassis includes a male luer lock adapter having external threads thereon, and a ferrule structure the lower end of which has a hollow sharpened lance. The apparatus is used with a syringe having a female luer lock connector which snap fits with the male luer lock adapter.

In use, the cap cover is opened, and a syringe is screwed onto the outer end of the adapter. The syringe is then tightened on the adapter which moves the lance downward and the lance penetrates the gasket on the vial thereby establishing flow communication with the content of the vial. The content of the vial is withdrawn by pulling back on the plunger of the syringe. The syringe is then removed with the content therein ready to receive a needle assembly for injecting the content into a patient.

U.S. Pat. No. 5,433,330 relates to a needleless access stopper used on containers with a cannula having a blunt, stopper penetrating tip.

The present invention provides sealing and access means for containers, such as bottles or vials made of glass or plastic containing medical fluids, such as x-ray contrast media and parenteral liquids. The access means provides for hermatic sealing, safe handling, sterilization and storing. The sealing means are designed for multiple use so that the medical fluid can be accessed repeatedly. After each withdrawal of the desired amount of the medical fluid, the sealing means self-seals itself thereby preventing contamination of the medical fluid by air-born particles, such as dust and bacteria. For convenience the invention will be described in combination with glass medicinal bottles. It is to be understood, however, that the invention includes sealing and access means for containers in general which comprise rigid or semi rigid access ports and are capable of receiving such sealing and access means.

SUMMARY OF THE INVENTION

In accordance with one aspect of the present invention, a universal closure assembly/container combination is provided to allow access to a medical fluid contained in the container with conventional access means available to healthcare professionals, such as iv tubing equipped with a luer connector or a syringe having sharp or blunt cannula or sharp or blunt spikes.

In another aspect, the present invention provides a method for repeatedly accessing a medical fluid contained in a container equipped with a universal closure assembly accessible with various access means available to healthcare and emergency practitioners and sometimes to patients requiring self-injections.

While the present invention provides access to medical fluids using various access means, it is preferred that the access means comprise no "sharps", such as in sharp needle cannulas, in order to prevent accidental injuries and transmittance of contagious diseases, such as AIDS.

The universal closure assembly/container combination comprises:

a) a container;

b) a closure assembly; and c) a removable cap covering the closure assembly.

The container is preferably made of glass, however, it can also be made of polymeric materials known in the art. The container has a neck portion terminating in an open end to receive the closure assembly which is inserted in the open end to seal the content therein and maintain it in sterile and aseptic condition.

The closure assembly comprises: an elastomeric stopper and a cylindrical collar. The stopper having a head portion and a skirt portion is made of an elastomeric base, such as a natural or synthetic rubber preferably having an inert, polymeric coating thereon covering at least the medical fluid contacting portions of the stopper. The coating may be of chlorobutyl rubber, polymeric fluorocarbon resins and thermoplastic films.

The elastomeric stopper is of cylindrical shape and has a flange head portion overlying the open top end of the container. Integral with the head portion is a skirt portion which extends into the open end and seated in the neck portion of the container, the diameter of the neck portion of the container being somewhat larger than the inside diameter of the skirt portion so that a tight seal is created between the skirt portion and the wall of the container.

In the center portion of the elastomeric stopper there is a cylindrical opening extending through the head and the skirt portions of the stopper. The cylindrical opening through the stopper body would expose the content of the container to the environment allowing contamination therefrom. In accordance with the present invention, the cylindrical opening is closed by a rupturable sealing membrane which is integral with the elastomeric stopper. However, the rupturable sealing membrane may also be made separately from the elastomeric stopper, positioned in the opening, and sealed into the elastomeric stopper using thermoplastic or other sealing means known in the art. Preferably, the elastomeric stopper and the sealing membrane are integral with each other and produced by blow molding or other suitable manufacturing techniques. The sealing membrane is a protuberance residing in the top half of head portion of the elastomeric stopper and is resembling an M-shaped configuration having: a flat, horizontal base open in its center portion; cylindrical side walls extending from the flat, horizontal base to the head top surface of the stopper; and a cup or U-shaped portion extending downwards and toward the bottom portion of the elastomeric stopper forming an M-shaped configuration when taken together with the cylindrical side walls. The rupturable sealing membrane is of thin, elastomeric material having a slit in its center portion which slit does not completely traverse the center portion of the rupturable sealing membrane.

The M-shaped sealing membrane in the elastomeric stopper would collapse, or at least deform when penetrated by a luer connector, sharp or blunt syringe cannula. For preventing such occurrence a rigid, cylindrical housing or male element, open at both ends are provided to support the M-shaped sealing membrane and also serving as a receiving means for an external female access means, such as a female luer connector. Such external access means are threaded into the male connecting means thereby rupturing the sealing membrane to establish fluid communication with the content of the container.

The cylindrical collar, preferably made of metal such as aluminum, is fastened over the elastomeric stopper and the neck portion of the container to securely hold the elastomeric stopper in the open end of the container. The cylindrical collar comprises a central opening in its flat top portion to allow access to the cylindrical opening in the stopper and to the sealing membrane and male element located in the cylindrical opening.

The removable cap covers the flat top and rim portions of the cylindrical collar and comprises retaining ears which engage the cylindrical collar to maintain the closure assembly in aseptic condition.

The method of accessing a medical fluid contained in a container equipped with the universal closure assembly of the present invention comprises the steps of:

a) providing the universal closure assembly/container combination of the present invention as described herein;

b) removing the removable cap from the flat top and rim portions of the cylindrical collar thereby exposing the sealing membrane and the male element or connecting means in the cylindrical opening of the elastomeric stopper; and c) accessing the medical fluid contained in the container by an access means.

The access means is preferably a syringe, cartridge or IV tubing having a female luer connector. However, other access means, such as a syringe having a sharp or blunt needle cannula or a spike may also be used to rupture the sealing membrane of the closure assembly.

BRIEF DESCRIPTION OF THE DRAWINGS

With reference to the annexed drawings, illustrating the invention.

DETAILED DESCRIPTION OF THE INVENTION

Figure 1B:
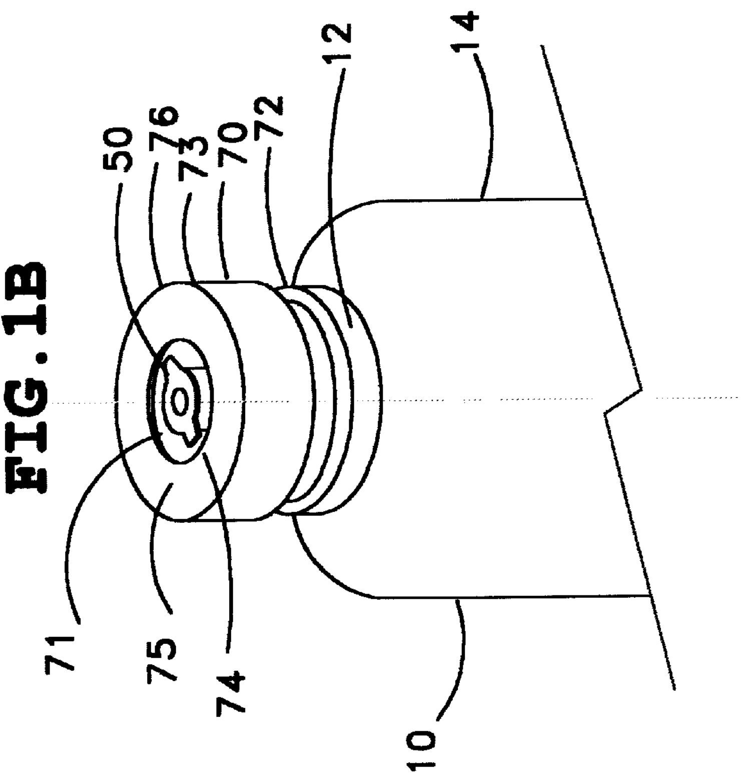
FIG. 1B is a perspective view of the container and the stopper with the multiple use access means shown in FIG. 1A without the cap.
Figure 1A:
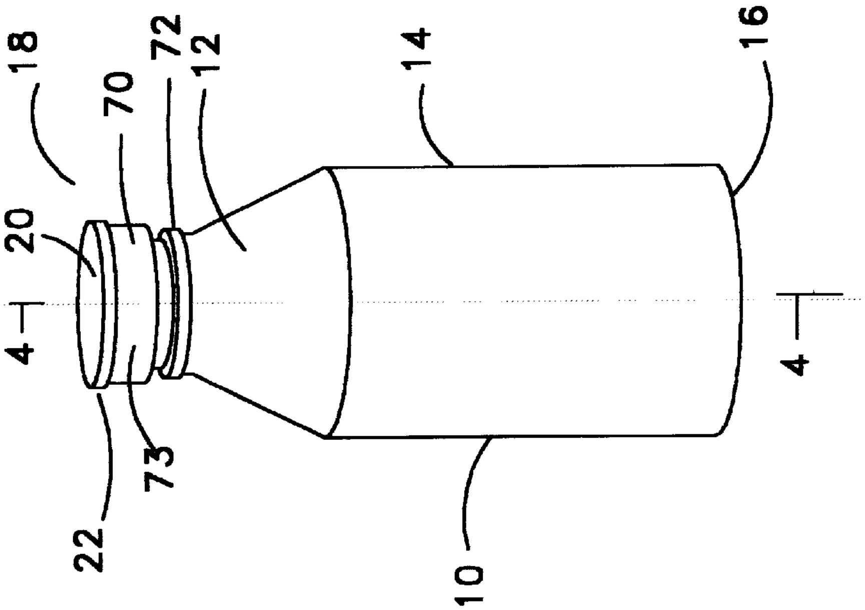
FIG. 1A is a perspective view of a container, a stopper with the multiple use access means, and a cap covering the access means.
Figure 2:
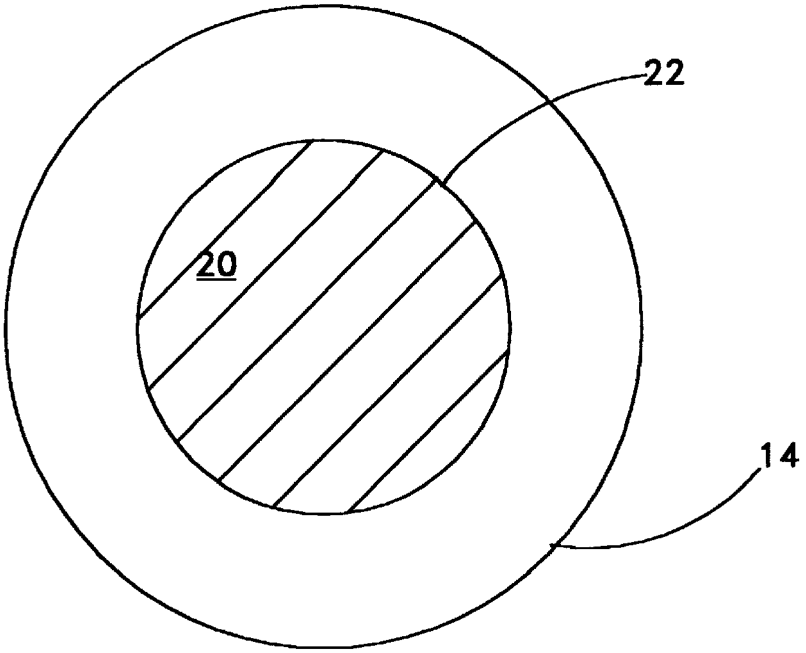
FIG. 2 is a top plan view of the container, the stopper with the multiple use access means, and the cap shown in FIG. 1A.
Figure 3:
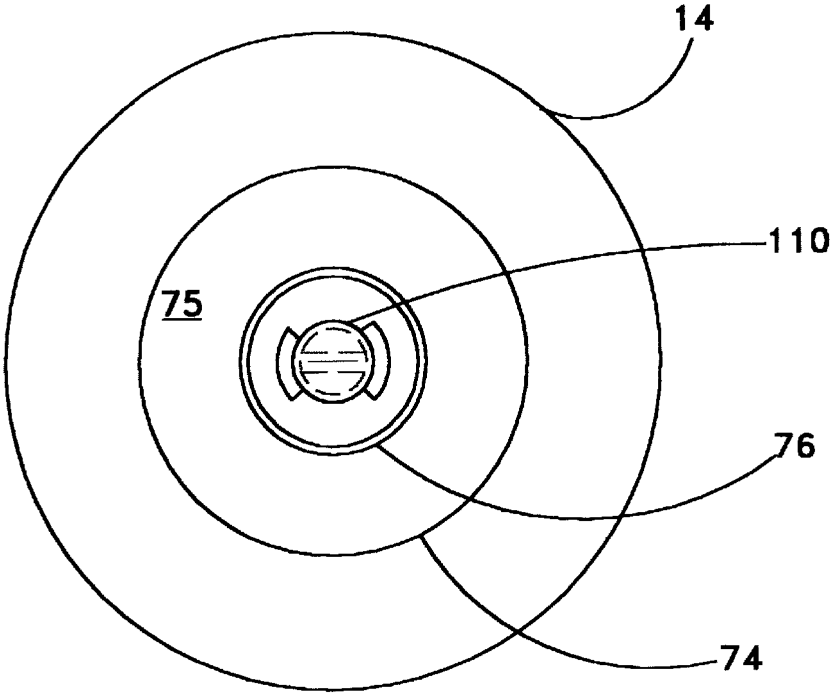
FIG. 3 is a top plan view of the container, the stopper with the multiple use access means without the cap thereon shown in FIG. 1B.

Referring to FIGS. 1A, 1B, 2, 3, 4, and 4A, the container 10 having an open end in which the multiple use universal stopper is used comprises a neck portion 12, a side portion 14, and a bottom portion 16. In the open end of neck portion 12 is located the multiple use universal stopper held securely in place by cylindrical collar 70 having an open area 71 in its top center portion, said open area being defined by the circular rim denoted by the numeral 74. Cylindrical collar further comprises a flat top surface 75 defined by circular rims 74 and 76 and top rim portion 73. Cylindrical collar 70 is crimped at its bottom rim 72 to neck portion 12 of the container. Flat top surface 75 is covered by a cylindrical, removable cap 18 which comprises a flat top portion 20, and a side rim portion 22 which overlaps top rim portion 73 of cylindrical collar 70. FIG. 1B shows locking ears 50 constituting a part of the universal stopper which is described later in reference to other Figures as the description of the invention proceeds.

Referring to FIGS. 1A, 1B, 5A and 5B, removable cap 18 covers flat top surface 75 and top rim portion 73 of cylindrical collar to maintain open area in top center portion 71 of cylindrical collar and locking ears 50 in aseption condition during storage. Removable cap 18 comprises: side rim portion 22, flexible retaining ears 24, and retainer button 26. When in place, retaining ears 24 are slid under circular rim 74 in cylindrical collar 70 providing a tight seal between remove cap 18 and flat top surface 75 of cylindrical collar. Retainer button 26 together with retaining ears 24 also serve to limit expansion of the thin elastomeric membrane or seal sterilization.

Figure 4:
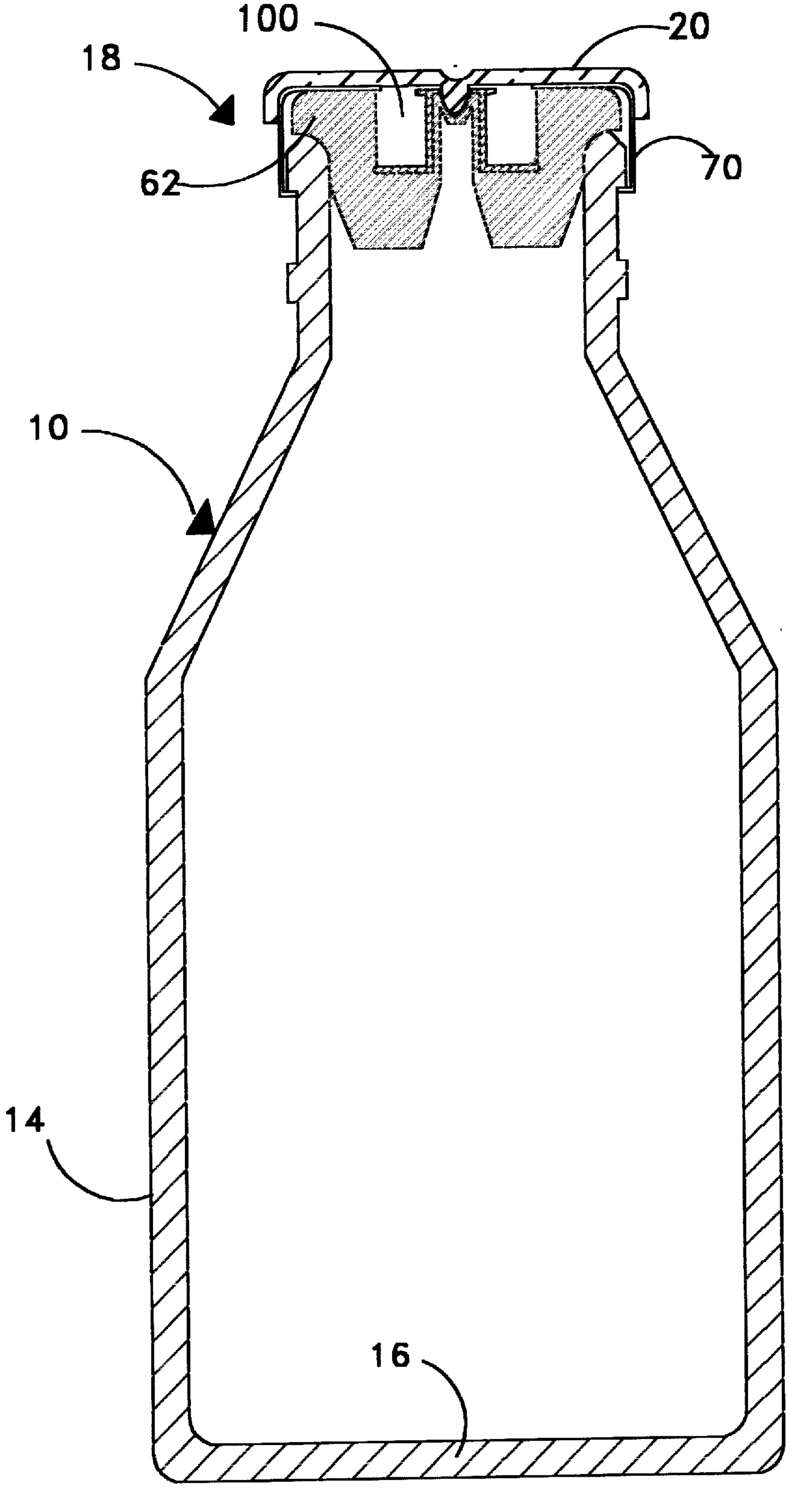
FIG. 4 is a cross-sectional view of the container, the stopper with the multiple use access means and the cap covering the access means taken along the line 4—4 of FIG. 1A.
Figure 4A:
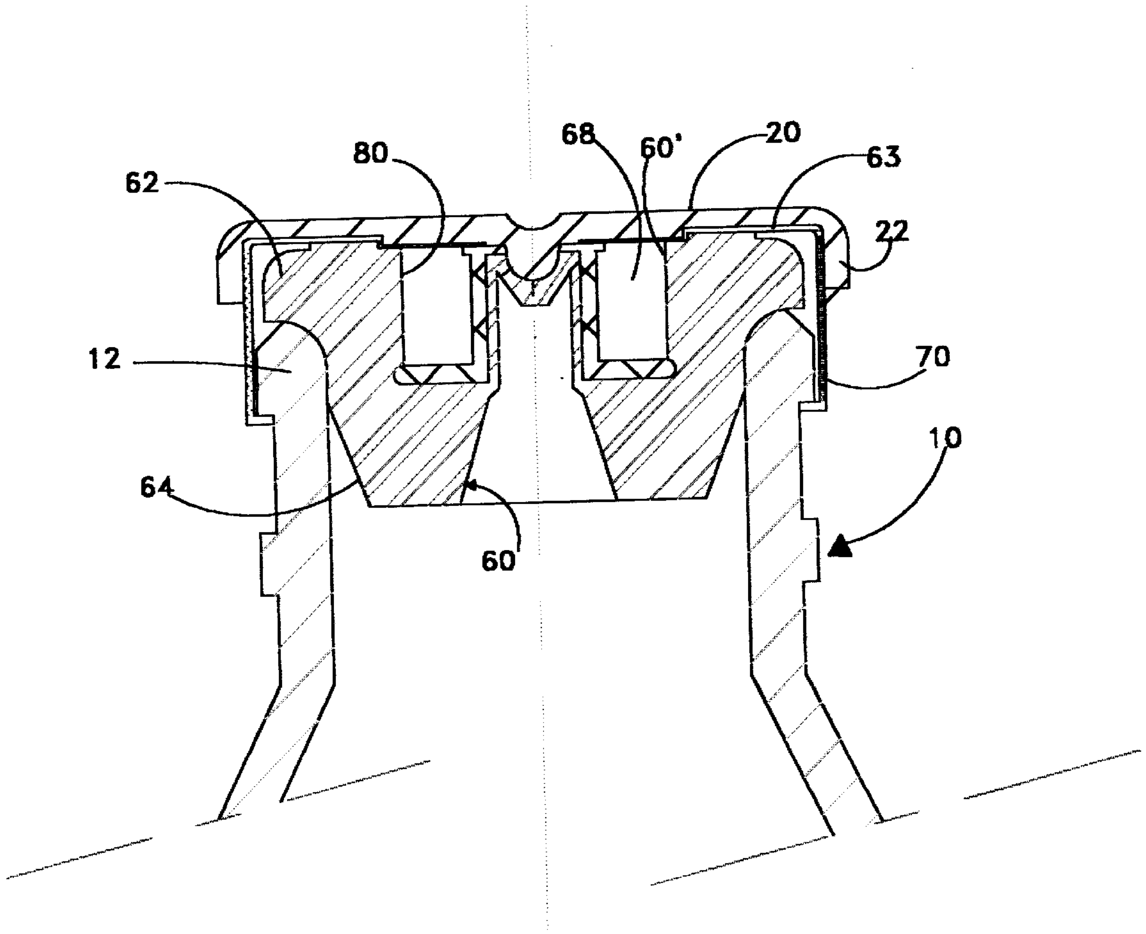
FIG. 4A is a greatly enlarged cross-sectional view of the top of the container, the stopper with the multiple use access means and cap shown in FIG. 4.
Figure 6:
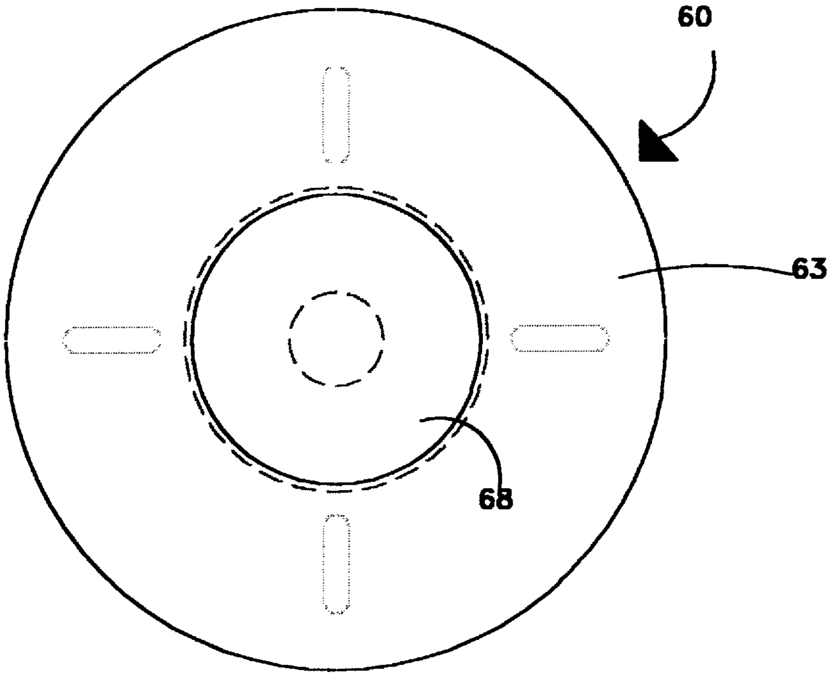
FIG. 6 is a top plan view of a prior art stopper designed to be pierced by a spike.
Figure 6A:
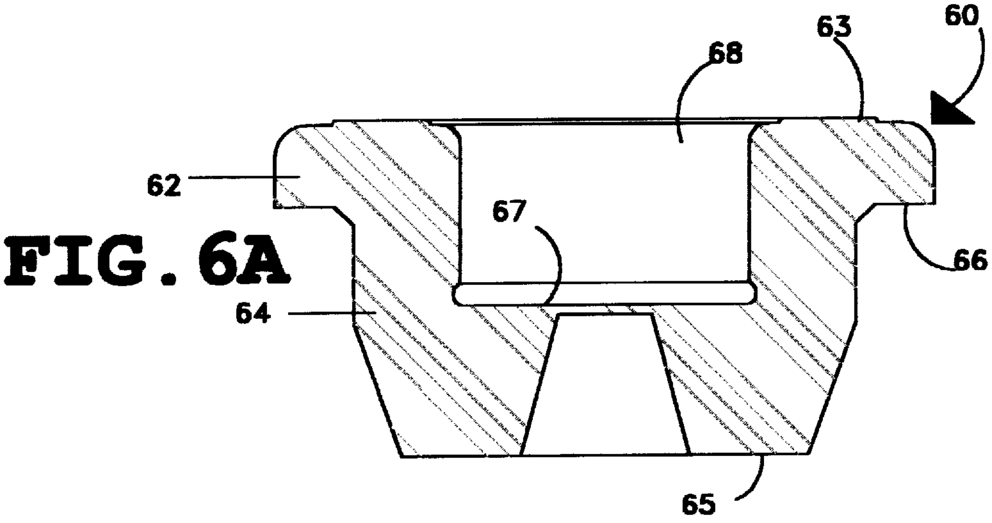
FIG. 6A is a cross-section of the prior art stopper of FIG. 6.
Figure 6B:
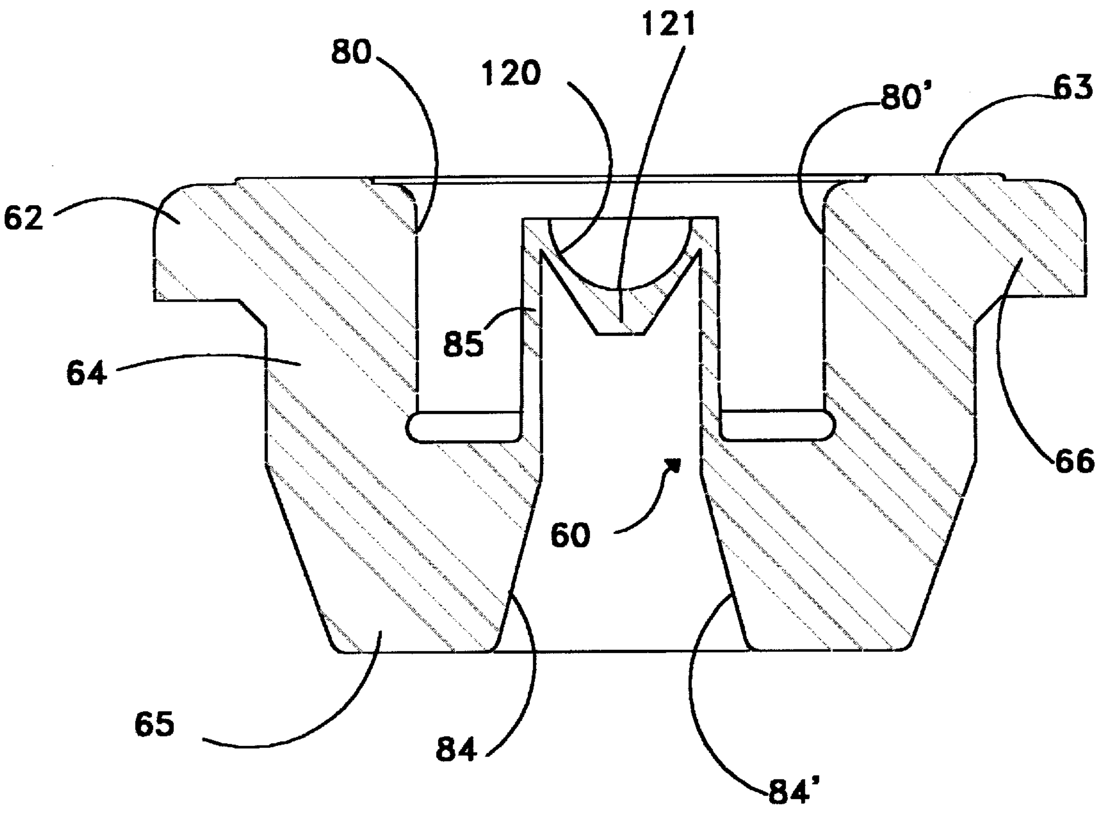
FIG. 6B is a cross-section of the stopper of the present invention having a cylindrical protuberance in the center therof which constitutes the seal or diaphragm in the stopper penetrable by various access means.
Figure 8:
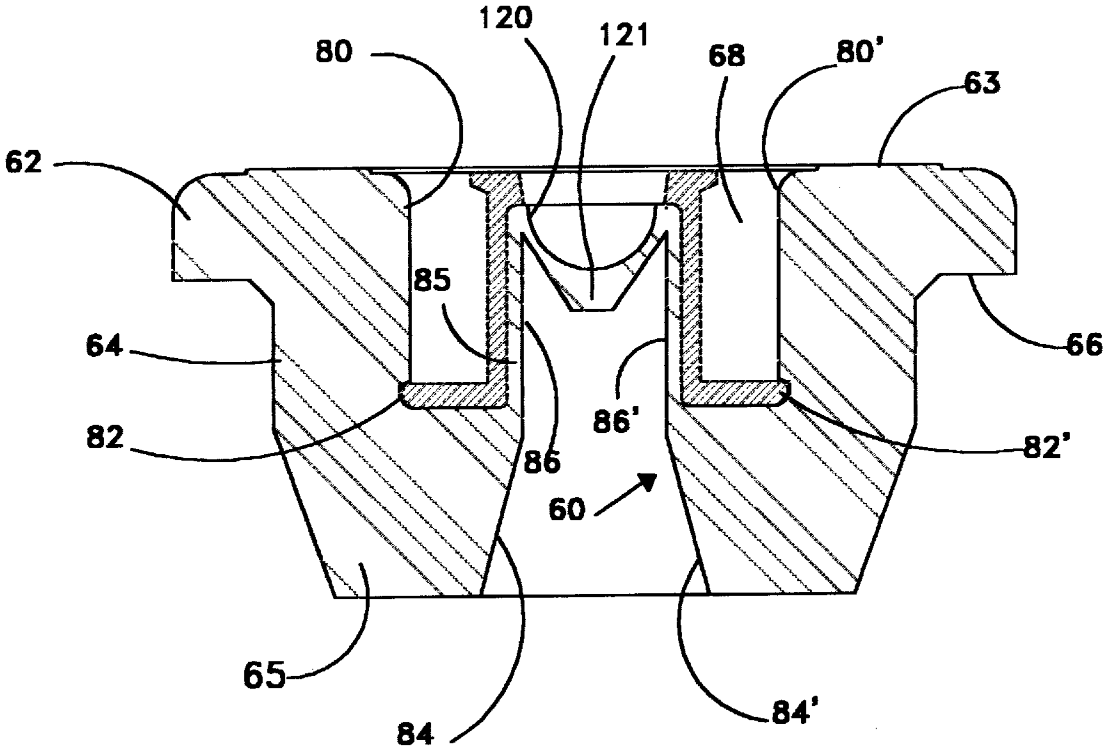
FIG. 8 is a cross-section of the stopper, the access means housing in the stopper and elastomeric seal or diaphragm supported by the housing.

Referring to FIGS. 1A, 1B, 4, 4A, 6, 6A, 6B and 8, the open end of the container 10 is to receive an elastomeric stopper 60 having a top surface 63 and a bottom surface 65 and comprises: a head 62 and a skirt 64 integral therewith. The head comprises a flange 66, extending laterally outwardly from skirt 64 and is designed to cover the transverse end surface of the container. The elastomeric stopper shown in FIGS. 6 and 6A is conventionally used by the prior art. In the present invention, as best seen in FIGS. 4A and 8, the elastomeric stopper further comprises: a cylindrical opening 68 in its center portion defined by cylindrical walls denoted by the numerals 80 and 80'; bottom ring portion denoted by the numerals 82 and 82'; and funnel shaped opening 83 extending downward from the bottom ring portion into the container defined by walls 84 and 84'. Projecting upward towards the top surface 63 of elastomeric stopper 60 is a hollow, vertically-oriented, cylindrical protuberance 85 defined by cylindrical walls 86 and 86' and top surface 120. Top surface 120, along with cylindrical walls 86 and 86', are designed to serve as the elastomeric seal in the elastomeric stopper. The cylindrical protuberance is preferably integral with the stopper body such as produced by blow molding technique or it may be produced separately and sealed into the central opening defined by walls 80 and 80' in the elastomeric stopper 60.

Figure 4C:
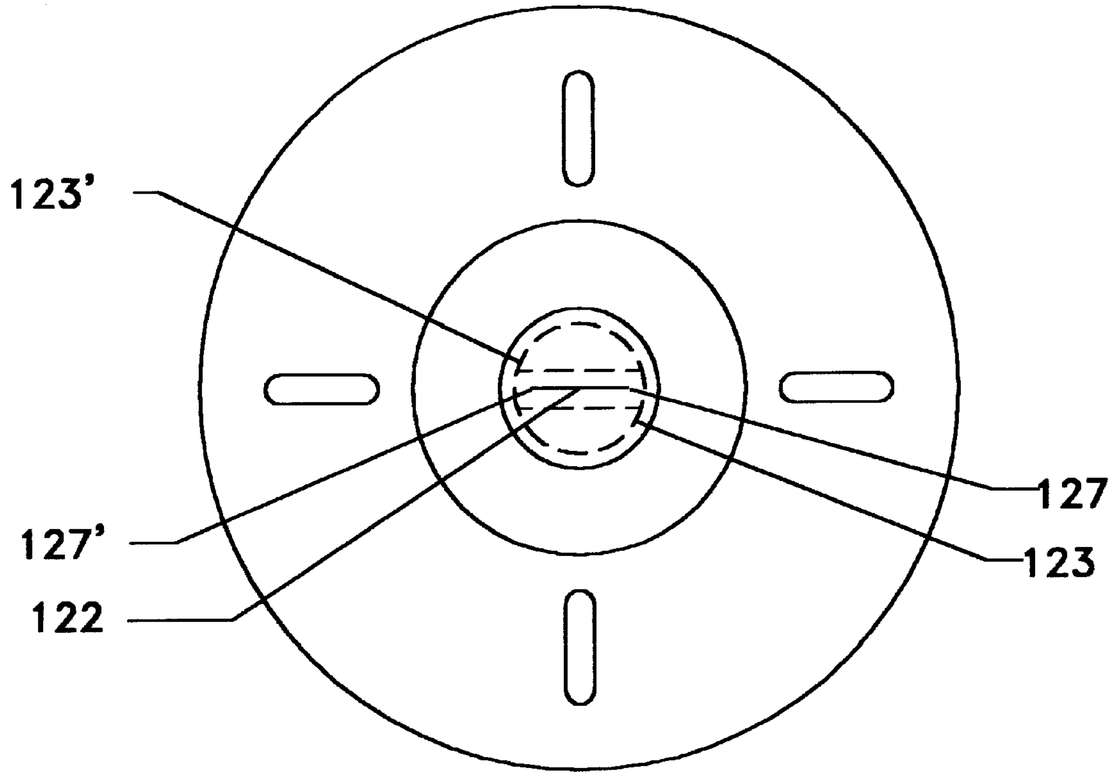
FIG. 4C is a top plan view of the M-shaped multiple use diaphragm shown in FIG. 4A.
Figure 4B:
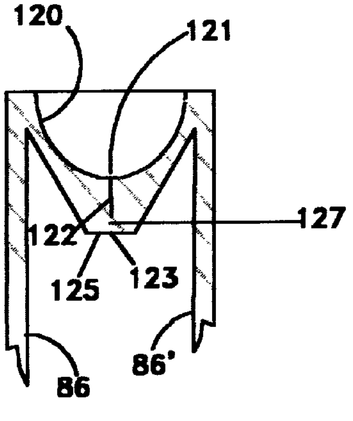
FIG. 4B is a greatly enlarged fragmentary cross-sectional view of the top of the M-shaped multiple use diaphragm shown in FIG. 4A constituting a component of the multiple use access means.
Figure 5A:
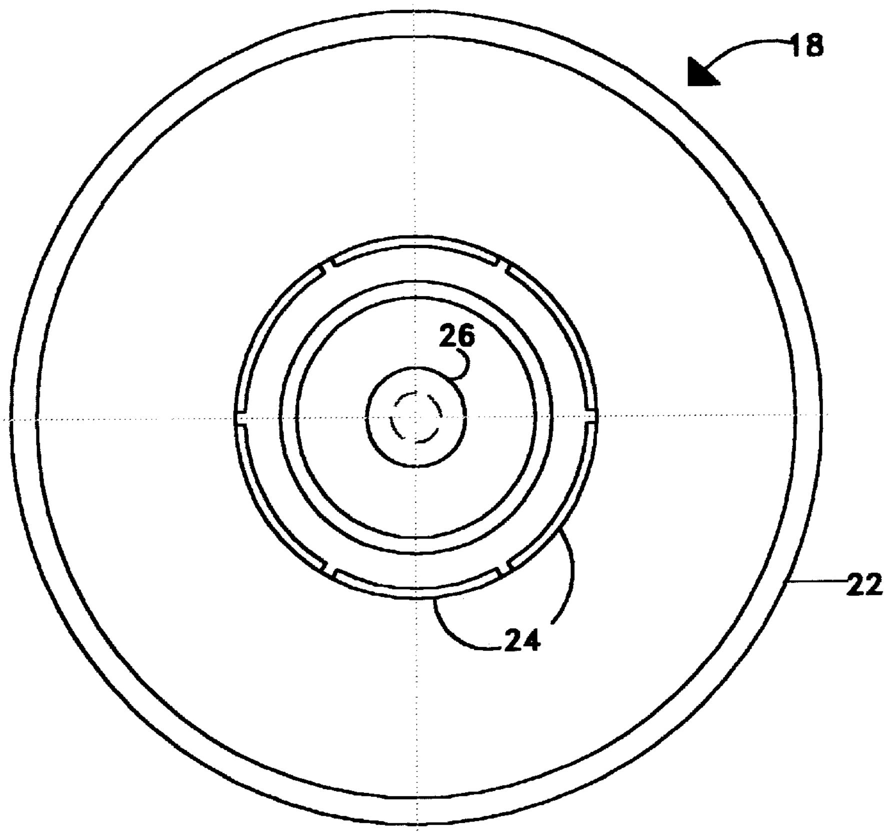
FIG. 5A is a bottom plan view of the cap removed from the container shown in FIG. 1A.
Figure 5B:
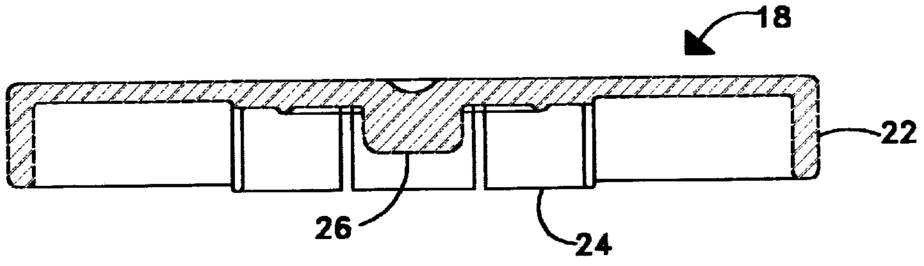
FIG. 5B is a sectional view of the of the cap removed from the container shown in FIG. 5A.

The vertically-oriented cylindrical protuberance is of thin, membrane-like material designed to be ruptured by an external force exerted on the protuberance by an access means, such as a luer connector. As best seen in FIGS. 4B and 4C showing in cross-sectional and top plan views, the cylindrical protuberance is an M-shaped diaphragm wherein the numerals 86 and 86' denote the leg portions and the numeral 120 denotes the top surface resembling a cup shape. The lowest point in the top surface 120 is denoted by the numeral 121 which is the center point in the cup-shaped portion. At the center point 121 there is provided a slit 122 extending from the top surface or inside surface toward the bottom surface 125 of the cup-shaped portion of the M-shaped diaphragm. The slit, however, does not penetrate the bottom surface 125. The thickness between the slit 122 and the intact bottom surface 125 is typically of form about 0.001 to about 2.0 mm. The unpenetrated portion of the membrane denoting its thickness at the center portion is denoted by the numeral 127 in FIGS. 4B and 4C. The unpenetrated membrane maintains the content of the container in sealed condition. In use, when this membrane is ruptured by an external access means, such as a needle cannula, luer connector or spike, fluid communication is established between the content of the container and the external access means. Upon disengaging the external access means for the multiple use universal stopper, the cup-shaped portion of the diaphragm reseals itself for the reason that the membrane is resilient and springs back to its original configuration. As a results the container is re-sealed until the fluid withdrawal process is repeated.

Figure 7A:
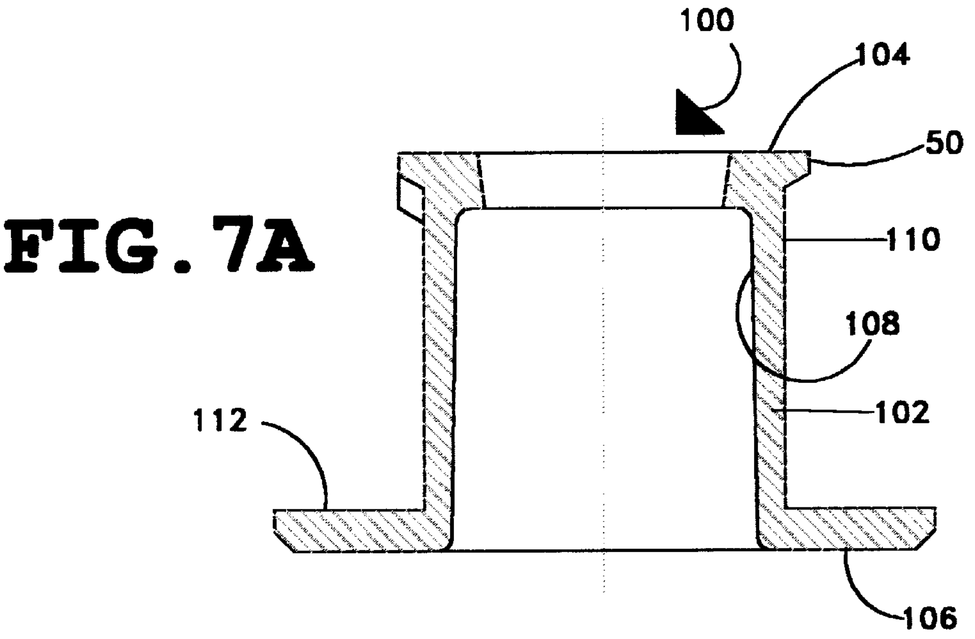
FIG. 7A is a cross-section of the multiple use access means housing.
Figure 7:
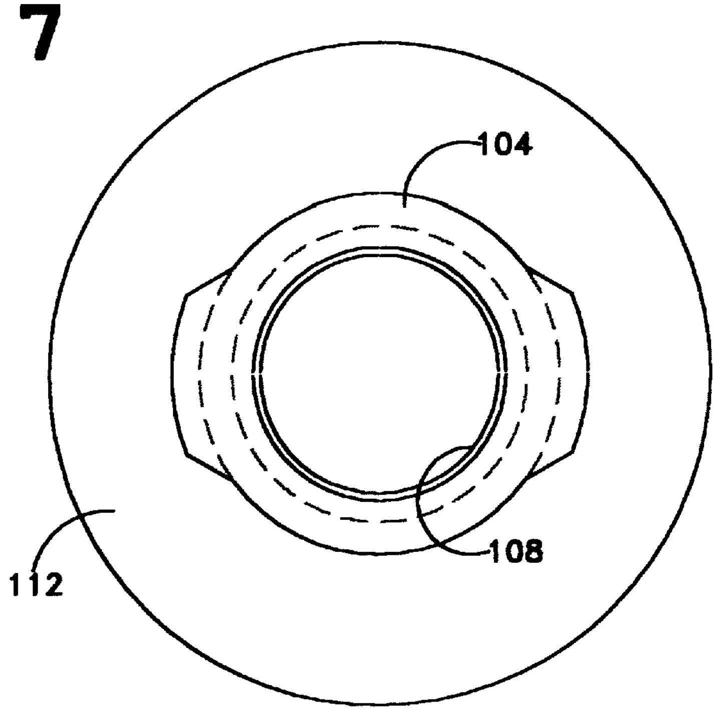
FIG. 7 is a top plan view of the multiple use access means housing.

In reference to FIGS. 7,7A and 8, in order to support vertically-oriented cylindrical protuberance 85 and to provide a means for receiving a male luer connector, a housing or male element generally designated as 100, is provided, located in the upper center portion 68 of elastomeric stopper 60. Housing 100 comprises: cylindrical wall 102 having a top surface 104 and bottom surface 106. Cylindrical wall 102 comprises an inside wall 108, an outside wall 110, locking ears 50, and horizontally-oriented bottom portion 112. Locking ears 50 is designed to securely hold the female element of a luer connector. Horizontally-oriented bottom portion 112 extends into the skirt 64 and sealed thereto at the bottom ring portion 82 and 82' of elastomeric stopper 60.

The cylindrical protuberance serving as a sealing membrane is of inert gas-impermeable polymeric material capable of flexing under internal or external pressures such as exerted during steam steriliztion. Preferably the membrane has a thickness of from about 0.001 mm to about 2.00 mm and a durometer of from about 25 to about 80 Shore A. Suitable elastomeric materials for constructing the membrane include:

natural rubber;

acrylate-butadiene rubber;

cis-polybutadiene;

chlorobutyl rubber;

chlorinated polyethylene elastomers;

polyalkylene oxide polymers;

ethylene vinyl acetate;

fluorosilicone rubbers;

hexafluoropropylene-vinylidene fluoride-tetrafluoroethylene terpolymers, such as sold under the tradenames of Fluorel and Viton;

butyl rubbers;

polyisobutene, such as sold under the tradename Vistanex;

synthetic polyisoprene rubber;

silicone rubbers;

styrene-butadiene rubbers;

tetrafluoroethylene propylene copolymers; and thermoplastic-copolyesters.

The cylindrical M-shaped protuberance is positioned in elastomeric stopper 60 so that its top surface 120 is spaced about 2 to 3 mm form retainer button 26 of removable cap 18 when the cap is placed on container 10. The spacing allows the membrane to flex outwardly under pressure, such as created under heat sterilization. However, spacing should not be more than about 2 to 3 mm so that under accidentally high pressures, bursting of the membrane is prevented by the retaining button 26 of removable cap 18.

Figure 9:
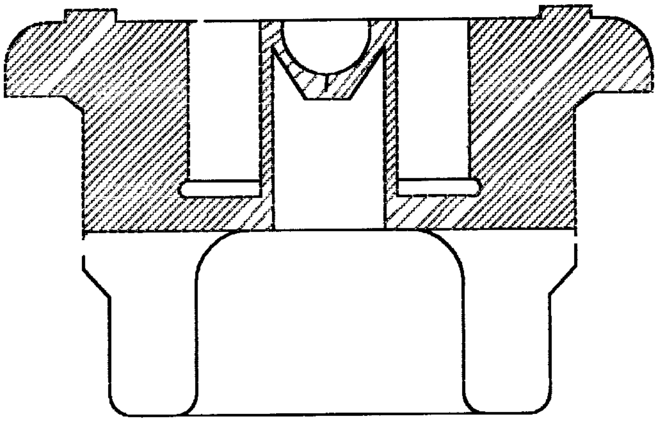
FIG. 9 is the cross-sectional view of a stopper used in lyophilization having the M-shaped multiple use diaphragm therein.
Figure 10:
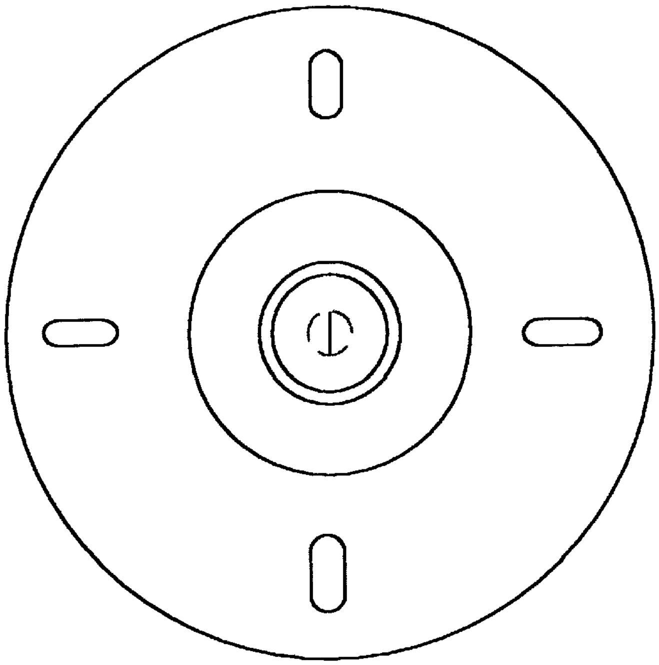
FIG. 10 is a top plan view of the stopper used in lyophilization having the U-shaped multiple use diaphragm therein shown in cross-sectional view in FIG. 9.

The multiple use universal stopper of the present invention may also have a configuration shown in FIGS. 9 and 10. The stopper of this configuration is used when lyophilization of the content of the container is desired. Prior to use the lyophilized content is reconstituted by injecting into the container through the multiple use universal stopper water, saline or other liquids.

Figure 11:
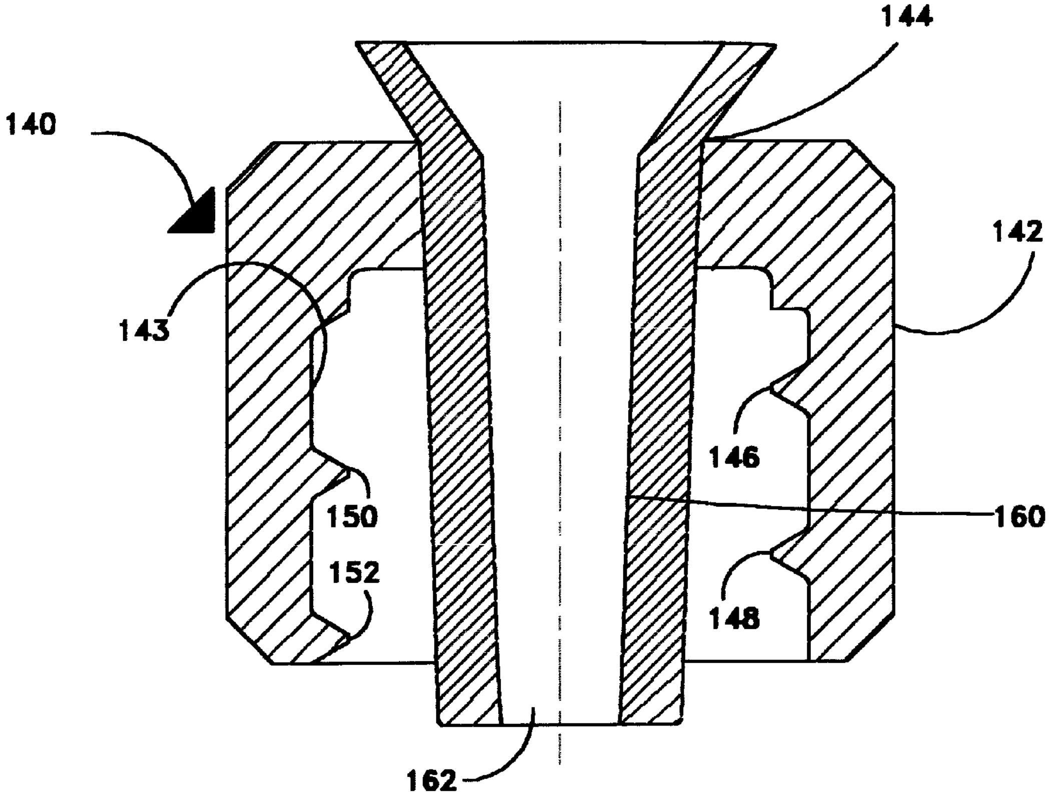
FIG. 11 shows a cross-section of a female luer connector with screw threads.

The universal stopper of the present invention is preferably used with a female luer connector when fluid communication is desired with the content of the container stoppered by the universal stopper. A typical female luer connector 140 is shown in FIG. 11 and comprises: cylindrical outside wall 142 and cylindrical inside wall 143 having an opening in their center portion for accommodating a tubing within the inside wall. Cylindrical ring 144 located in the top center portion of cylindrical inside wall 143 tightly holds tubing 160 which has a fluid communicating channel 162. Cylindrical inside wall 143 further comprises integral screw threads 146, 148, 150 and 152 which, upon connecting the female luer connector to the male luer connector, engages locking ears 50 on the housing or male element 100, as shown in FIGS. 7 and 7A. Other type of female luer connectors, such as snap-on connectors may also be used.

Figure 12:
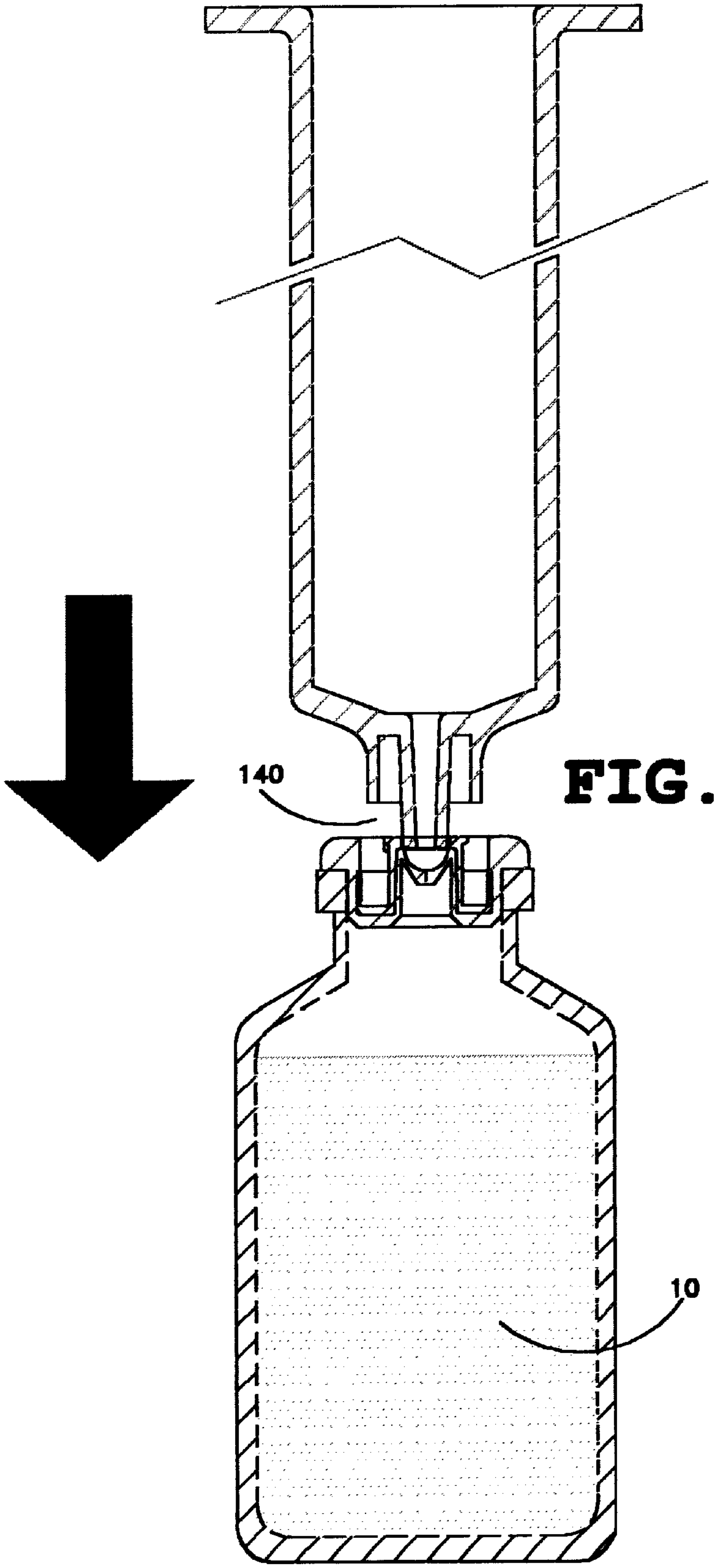
FIG. 12 is a cross-section of a female luer connector which is to engage access means housing shown in FIGS. 7,7A and 8, wherein the female luer connector and access means housing are shown prior to their engagement.

FIG. 12 shows, in cross-sectional view, a syringe having a female luer connector, which is to engage the multiple use universal stopper in the container 10, wherein the syringe and universal stopper are shown prior to their engagement. When it is desired to deliver medical fluid from container 10 to a patient, removable cap 18 is removed by an upward manual pressure exerted on its rim portion 22 thereby exposing locking ears 50 of the access means housing.

If the female luer connector of FIG. 11 is used, it is attached to the multiple use universal stopper by twisting motion wherein threads 146, 148, 150 and 152 engage locking ears 50 of access means housing 100. Upon turning the female luer connector 140, end portion of tubing 160 ruptures membrane of the universal stopper to establish fluid communication with the content of the container.

Figure 12A:
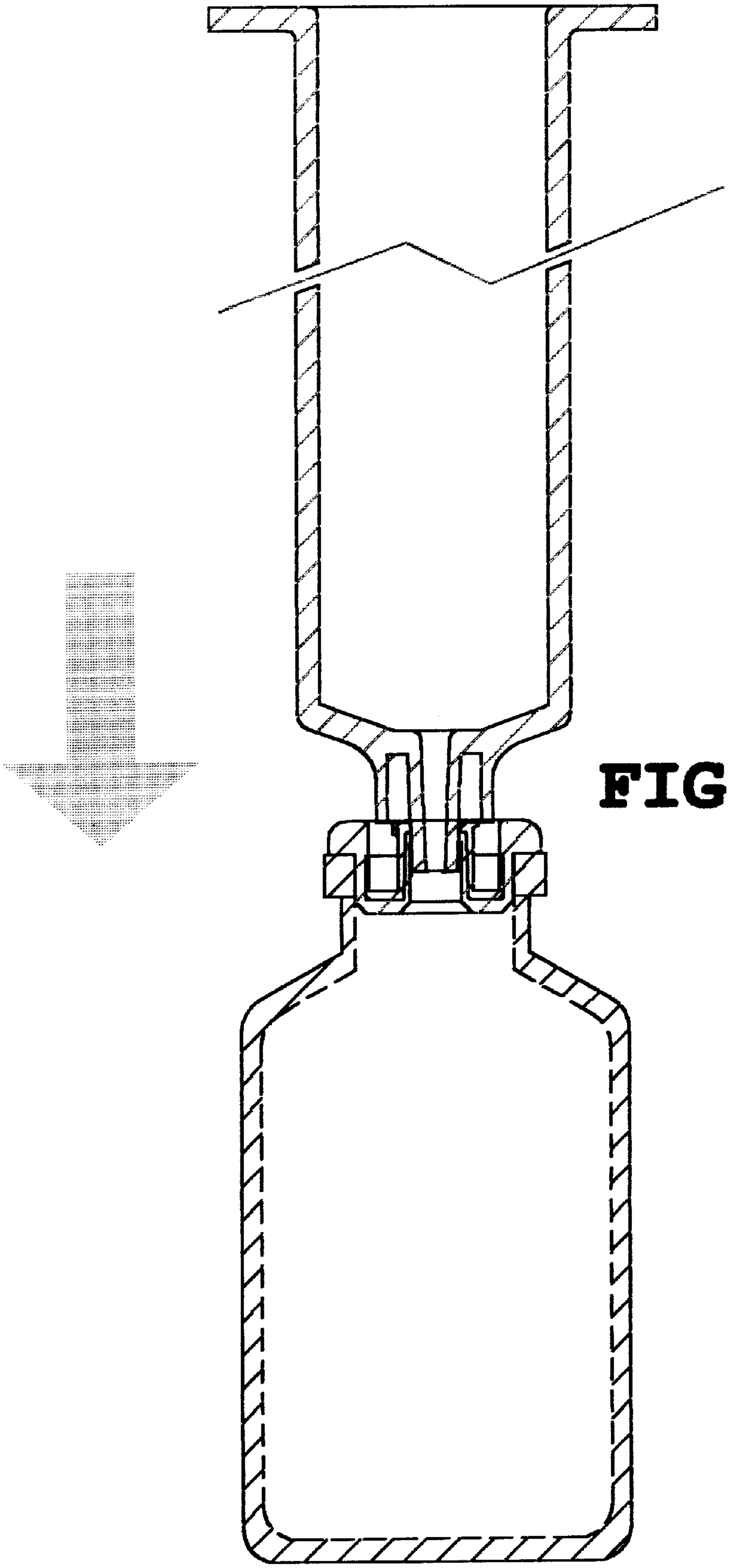
FIG. 12A is a cross-section of the female luer connector partially engaging access means housing and rupturing the elastomeric seal shown in FIG. 12.

FIG. 12A shows, in cross-sectional view, the syringe having the female luer connector partially engaging the multiple use universal stopper.

Figure 12B:
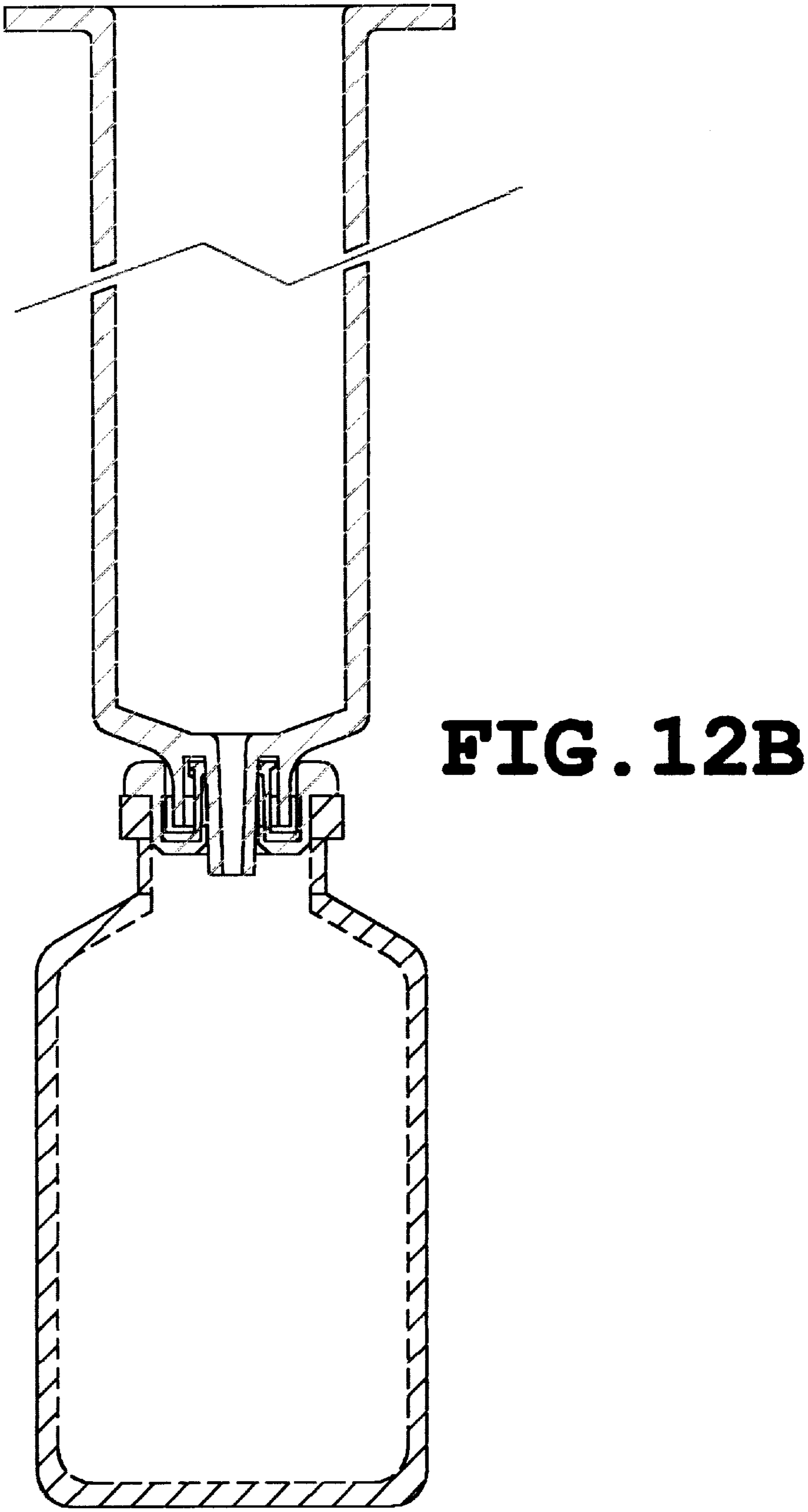
FIG. 12B is a cross-sectional view of the female luer connector completely engaging access means housing.

FIG. 12B shows, in cross-sectional view, the syringe having the female luer connector completely engaging the multiple use universal stopper.

Figure 13:
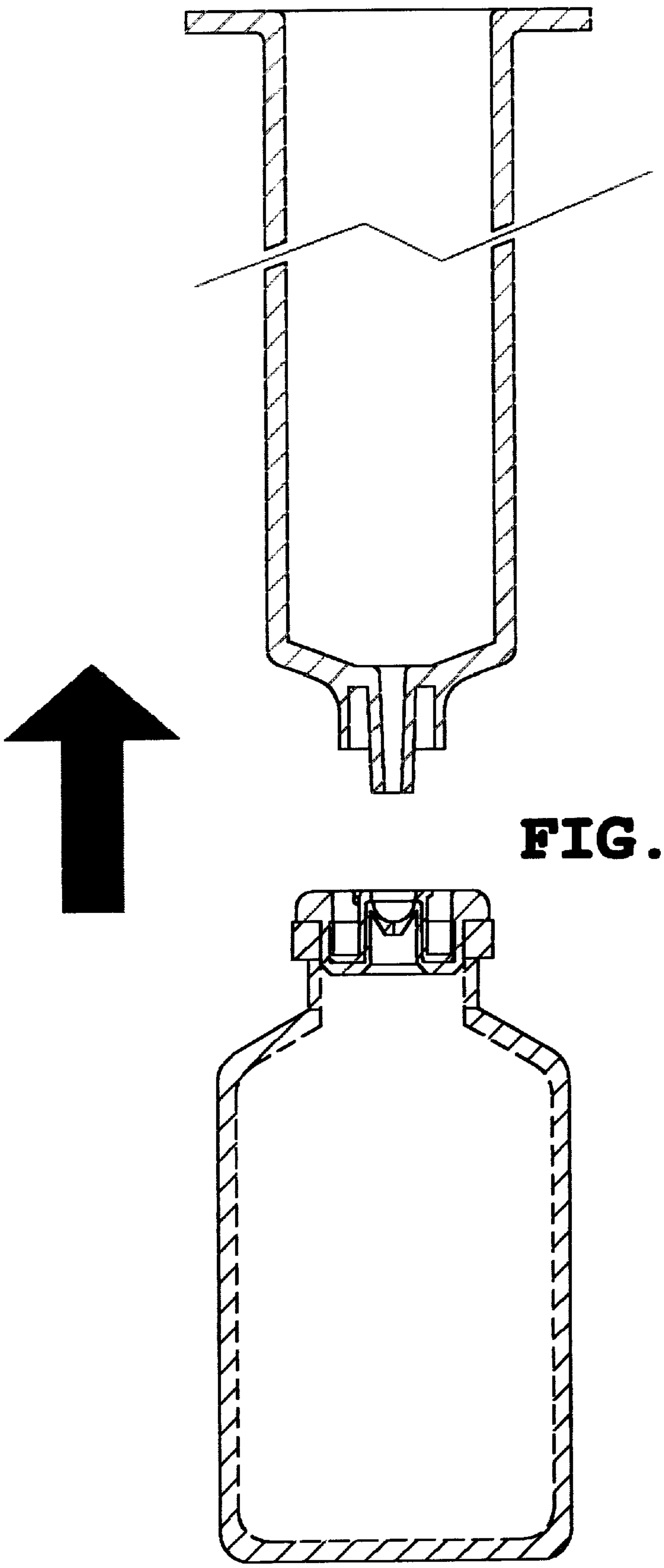
FIG. 13 is a cross-sectional view of the female luer connector disengaging access means housing.

FIG. 13 shows, in cross-sectional view, the syringe having the female luer connector removed from the multiple use universal stopper after their engagement.

The multiple use universal stopper can be engaged by a female luer connector having a blunt end which engages and ruptures the cylindrical M-shaped seal in the center of the multiple use universal stopper. However, the multiple use universal stopper also allows access to the content of the container by a sharp or blunt needle cannula or a spike.

Materials of Construction and Use

The elastomeric stopper used in conjunction with the universal stopper of the present invention is fluid impervious, resilient, and inert without leachable additives therein in order to prevent any alteration of the product contained in the container. It may be of a single component or a blend of components. Examples of materials include synthetic and natural rubbers, such as butyl rubber, isoprene rubber, silicone rubber, halogenated rubber, ethylene propylene therpolymer and the like. Specific examples of a synthetic elastomeric rubber include the $CH_2CF_2$—$C_3F_6$ ($C_3F_5H$) and the $C_2F_4$—$C_2F_3OCF_3$ series of elastomers made by DuPont under the trade names of VITON® and CARLEZ®; the fluoro-silicone rubbers, such as those made by Dow Corning under the trade name of SILASTIC®; and polyisobutylenes, such as VISTANEX MML-100 and MML-140; and halogenated butyl rubber, such as CHLOROBUTYL 1066, made by Exxon Chemical Company.

These or other suitable elastomers may be made into the desired stopper configuration by known methods. Such methods conventionally include the use of a curing agent, a stabilizer and a filler and comprise a primary and a secondary curing step at elevated temperatures.

The container used in conjunction with the present invention may be of glass or a polymeric material, i.e., plastic, which are well known in the pharmaceutical industry. When the container is made of glass, it is in the shape of a vial or bottle. The vial or bottle is of rigid or semi-flexible polymeric material. In all shapes the container is provided with a neck portion which is rigid and retains its configuration so that it is capable of being hermetically sealed by the elastomeric universal stopper of the present invention. The container may have a volume capacity of from 5 ml to 1000 ml or more, preferably about 10 ml to 500 ml.

The mouth of the container is to receive the multiple use universal stopper. The external diameter of the stopper is slightly larger than the internal diameter of the neck of the container so that on insertion of the multiple use universal stopper into the mouth of the container, a tight, hermetic seal is achieved.

The cylindrical collar is preferably made of metal, such as aluminum, while the housing is made of hard plastic known by the prior art and used in conjunction with pharmaceutical fluids.

Prior to use, the container and component parts of the closure are sterilized and the container is filled with a pharmaceutical fluid, such as a parenteral solution. The multiple use universal stopper is inserted, hermetically sealing the content of the container. Cylindrical collar is then crimped onto the container to securely hold the multiple use universal stopper in the container. Lastly, the removable cap is snapped onto the cylindrical collar to complete the closing of the container.

| PARTS LIST | |
|---|---|
| Container | 10 |
| Neck portion of container | 12 |
| Side portion of container | 14 |
| Bottom portion of container | 16 |
| Removable cap | 18 |
| Flat top portion of removable cap | 20 |

-continued

| PARTS LIST | |
|---|---|
| Side rim portion of removable cap | 22 |
| Flexible retaining ears | 24 |
| Retainer button | 26 |
| Locking ears | 50 |
| Elastomeric stopper | 60 |
| Head of elastomeric stopper | 62 |
| Top surface of elastomeric stopper | 63 |
| Skirt of elastomeric stopper | 64 |
| Bottom surface of elastomeric stopper | 65 |
| Flange of elastomeric stopper | 66 |
| Elastomeric seal in prior art stopper | 67 |
| Cylindrical opening in elastomeric stopper | 68 |
| Cylindrical collar on container | 70 |
| Open area in top center portion of cylindrical collar | 71 |
| Top rim portion of cylindrical collar | 73 |
| Open area in top center portion of cylindrical rim | 74 |
| Flat top surface of cylindrical collar | 75 |
| Funnel-shaped opening in skirt of elastomeric stopper | 83 |
| Circular rims defining flat top surface of cylindrical collar | 74, 76 |
| Cylindrical walls defining the cylindrical opening in elastomeric stopper | 80, 80' |
| Bottom ring portion in the opening of elastomeric stopper defined by Funnel-shaped opening in skirt of elastomeric stopper | 82, 82' 83 |
| Walls of funnel-shaped opening | 84, 84' |
| Cylindrical protuberance constituting the seal in elastomeric stopper | 85 |
| Walls of cylindrical protuberance | 86, 86' |
| Housing of male element | 100 |
| Cylindrical wall of housing | 102 |
| Top surface of housing | 104 |
| Bottom surface of housing | 106 |
| Inside wall of housing | 108 |
| Outside wall of housing | 110 |
| Horizontally oriented bottom portion of housing | 112 |
| Inside surface membrane of M-shaped diaphragm | 120 |
| Center of inside surface membrane of M-shaped diaphragm | 121 |
| Slit in cup-shaped portion of M-shaped diaphragm | 122 |
| Boffom surface of cup-shaped portion of M-shaped diaphragm | 125 |
| Thickness of unpenetrated membrane at center portion | 127 |
| Female luer connector | 140 |
| Cylindrical outside wall of female luer connector | 142 |
| Cylindrical inside wall of female luer connector | 143 |
| Cylindrical ring of fernale luer connector | 144 |
| Integral screw threads in inside wall of female luer connector | 146, 148, 150, 152 |
| Tubing in female luer connector | 160 |
| Fluid communicating channel in tubing | 162 |

The present invention has been described in connection with the preferred embodiment shown in the drawings however, various changes and modifications will be apparent to those skilled in the art.

What is claimed is:

1. A universal closure assembly and a container combination, said combination comprising:

(a) a container;

(b) a closure assembly; and (c) a removable cap covering said closure assembly; wherein said container (a), containing a medical fluid therein, having a neck portion terminating in an open end;

said closure assembly (b), inserted into the open end of said container comprises:

(1) an elastomeric stopper for hermetically sealing the container at its open end comprising:

a head portion;

a skirt portion;

a cylindrical opening in a center portion of said head and skirt portions;

a hollow, vertically oriented thin elastomeric protuberance serving as a diaphragm for sealing the opening in the center portion of the elastomeric stopper designed to be ruptured by an external force, said elastomeric protuberance having a generally M-shaped configuration comprising: a flat, horizontal base open in its center portion; cylindrical side walls extending from the flat, horizontal base to the top surface of said stopper; a cup-shaped portion extending downwards from the top of the cylindrical walls, said cup-shaped portion having a slit in its center portion extending towards the content of the container without traversing said diaphragm;

(2) a rigid, cylindrical housing having open ends enclosing said vertically oriented thin elastomeric protuberance to support said vertically oriented thin elastomeric protuberance and to serve as means for receiving and engaging a female luer connector whereby an external force moves the female luer connector which penetrates the thin elastomeric protuberance to establish fluid communication with the medical fluid contained in said container, said rigid cylindrical housing comprising: cylindrical walls having a top portion and a bottom portion, said top portion having locking ears designed to hold the female element of the luer connector, and said bottom portion sealed in the skirt portion of the elastomeric stopper;

(3) a cylindrical collar fastened over a portion of the elastomeric stopper and neck portion of the container to securely hold the elastomeric stopper in the open end of the container, said cylindrical collar having a central opening in its float top portion to allow access to the elastomeric protuberance and the rigid cylindrical housing located in the center portion of said elastomeric stopper; and said removable cap (c) covering the flat top and rim portions of said cylindrical collar comprising retaining ears engaging said cylindrical collar to maintain said closure assembly in aseptic condition.

2. The universal closure assembly and the container combination of claim 1 wherein said vertically oriented thin elastomeric protuberance is integral with said elastomeric stopper.

3. The universal closure assembly and the container combination of claim 1 wherein said vertically oriented cylindrical protuberance is of inert, gas impermeable polymeric material selected from the group consisting of:

natural rubber;
acrylate-butadiene rubber;
cis-polybutadiene;
chlorobutyl rubber;
chlorinated polyethylene elastomers;
polyalkylene oxide polymers;
ethylene vinyl acetate;
fluorosilicone rubbers;
hexafluoropropylene-vinylidene fluoride-tetrafluoroethylene terpolymers;
butyl rubbers;
polyisobutene;
synthetic polyisoprene rubber;
silicone rubbers;
styrene-butadiene rubbers;
tetrafluoroethylene propylene copolymers; and
thermoplastic-copolyesters.

4. The universal closure assembly and the container combination of claim 1 wherein said vertically oriented cylindrical protuberance has a thickness of from about 0.001 mm to about 1.00 mm and a durometer of from about 25 to about 80 Shore A.

5. The universal closure assembly and the container combination of claim 1 wherein said vertically oriented cylindrical protuberance reseals itself after puncture by a fluid access means.

6. The universal closure assembly and the container combination of claim 1 is used for lyophilizing the fluid contained in said container.

7. The universal closure assembly and the container combination of claim 1 wherein said container is made of glass.

8. The universal closure assembly and the container combination of claim 1 wherein said container is a vial.

9. The universal closure assembly and the container combination of claim 1 wherein said container is a bottle.

10. The universal closure assembly and the container combination of claim 1 wherein said container is made of a polymeric material.

11. The universal closure assembly and the container combination of claim 1 wherein said medical fluid is a parenteral liquid.

12. The universal closure assembly and the container combination of claim 11 wherein said parenteral liquid is an x-ray contrast medium.

13. The universal closure assembly and the container combination of claim 11 wherein said parenteral liquids a therapeutic liquid.

14. The universal closure assembly and the container combination of claim 1 wherein said volume capacity of said container is of from about 5 ml to about 1000 ml.

15. A method of accessing a medical fluid contained in a container equipped with a universal closure assembly comprising the steps of:

(A.) providing the universal closure assembly and the container combination comprising:
(a) a container;
(b) a closure assembly; and
(c) a removable cap covering said closure assembly;

wherein said container (a), containing a medical fluid therein, having a neck portion terminating in an open end;

said closure assembly (b), inserted into the open end of said container comprises:

(1) an elastomeric stopper for hermetically sealing the container at its open end comprising:
a head portion;
a skirt portion;
a cylindrical opening in a center portion of said head and skirt portions;
a hollow, vertically oriented thin elastomeric protuberance serving as a diaphragm for sealing the opening in the center portion of the elastomeric stopper designed to be ruptured by an external force, said elastomeric protuberance having a generally M-shaped configuration comprising: a flat, horizontal base open in its center portion; cylindrical side walls extending from the flat, horizontal base to the top surface of said stopper; a cup-shaped portion extending downwards from the top of the cylindrical walls, said cup-shaped portion having a slit in its center portion extending towards the content of the container without traversing said diaphragm;

(2) a rigid, cylindrical housing having open ends enclosing said vertically oriented thin protuberance to support said vertically oriented thin elastomeric protuberance and to serve as means for receiving and twistably engaging a female luer connector whereby an external force moves the female luer connector which penetrates the thin elastomeric protuberance to establish fluid communication with the medical fluid contained in said container, said rigid cylindrical housing comprising: cylindrical walls having a top portion and a bottom portion, said top portion having locking ears designed to hold the female element of the luer connector, and said bottom portion sealed into the skirt portion of the elastomeric stopper;

(3) a cylindrical collar fastened over a portion of the elastomeric stopper and neck portion of the container to securely hold the elastomeric stopper in the open end of the container, said cylindrical collar having a central opening in its flat top portion to allow access to the elastomeric protuberance and the rigid cylindrical housing located in the center portion of said elastomeric stopper; and said removable cap (c) covering the flat top and rim portions of said cylindrical collar comprising retaining ears engaging said cylindrical collar to maintain said closure assembly in aseptic condition;

(B.) removing said removable cap from said flat top and rim portions of said cylindrical collar; and (C.) accessing the medical fluid contained in said container by an access means with said female luer connector.

16. The method of claim 15 wherein said access means with said female luer connector comprising:

(a) a cylindrical cap having thread means on the inside wall thereof;

(b) a tubing conduit having a fluid channel therein contained in said cylindrical cap and permanently attached to said cap by sealing means, wherein one end of the tubing conduit extends beyond the bottom rim portion of said cap and is designed to contact and rapture the vertically oriented thin elastomeric protuberance when said cylindrical cap is threaded onto said universal closure assembly to establish fluid communication with the content of the container.

17. The method of claim 6 wherein said access means is a syringe having a sharp or blunt needle cannula or a sharp or blunt spike.

18. The method of claim 15 wherein said vertically oriented thin elastomeric protuberance has a thickness of from about 0.001 mm to about 1.00 mm and a durometer of from about 25 to about 80 Shore A.

19. The method of claim 15 wherein said vertically oriented thin elastomeric protuberance is of an elastomeric material selected from the group consisting of:

natural rubber;
acrylate-butadiene rubber;
cis-polybutadiene;
chlorobutyl rubber;
chlorinated polyethylene elastomers;
polyalkylene oxide polymers;
ethylene vinyl acetate;
fluorosilicone rubbers;
hexafluoropropylene-vinylidene fluoride-tetrafluoroethylene terpolymers;
butyl rubbers;
polyisobutene;
synthetic polyisoprene rubber;
silicone rubbers;
styrene-butadiene rubbers;
tetrafluoroethylene propylene copolymers; and
thermoplastic-copolyesters.

20. The method of claim 15 wherein said medical fluid is a therapeutic liquid.

21. The method of claim 15 wherein said medical fluid is a diagnostic liquid.

22. The method of claim 16 wherein said medical fluid is a nutritional liquid.

* * * * *